US009907471B2

(12) United States Patent
Caves et al.

(10) Patent No.: US 9,907,471 B2
(45) Date of Patent: Mar. 6, 2018

(54) VISUALIZATION OF HEART WALL TISSUE

(71) Applicant: The Board of Trustees of the Leland Stanford Junior University, Palo Alto, CA (US)

(72) Inventors: Jeffrey Caves, Palo Alto, CA (US); Paul J. Wang, Saratoga, CA (US); Joyce E. Farrell, Palo Alto, CA (US); Brian A. Wandell, Menlo Park, CA (US); Henryk Blasinski, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 177 days.

(21) Appl. No.: 14/509,923

(22) Filed: Oct. 8, 2014

(65) Prior Publication Data
US 2015/0099979 A1 Apr. 9, 2015

Related U.S. Application Data

(60) Provisional application No. 61/888,208, filed on Oct. 8, 2013.

(51) Int. Cl.
*A61B 5/00* (2006.01)
*A61B 5/02* (2006.01)

(52) U.S. Cl.
CPC .......... *A61B 5/0044* (2013.01); *A61B 5/0071* (2013.01); *A61B 5/0075* (2013.01); *A61B 5/0084* (2013.01); *A61B 5/4848* (2013.01); *A61B 5/02028* (2013.01); *A61B 5/748* (2013.01); *A61B 5/7425* (2013.01)

(58) Field of Classification Search
CPC ... A61B 5/0044; A61B 5/0071; A61B 5/0075; A61B 5/0084; A61B 5/02028; A61B 5/4848; A61B 5/7425; A61B 5/748
See application file for complete search history.

(56) References Cited

U.S. PATENT DOCUMENTS 4,785,806 A 11/1988 Deckelbaum
5,350,375 A 9/1994 Deckelbaum et al.
(Continued)

OTHER PUBLICATIONS

Mercader et al., "Use of endogenous NADH fluorescence for real-time in situ visualization of epicardial radiofrequency ablation lesions and gaps." Am J Physiol Heart Circ Physiol; 302(10):H2131-8, 2012.
(Continued)

*Primary Examiner* — Michael Rozanski
(74) *Attorney, Agent, or Firm* — Crawford Maunu PLLC

(57) ABSTRACT

Various aspects of the instant disclosure are directed to imaging tissue. As may be implemented in accordance with one or more embodiments, aspects of the present disclosure are directed to apparatuses and methods involving the following. A light source includes an array of light emitters that illuminate a tissue region of a heart wall with light at different wavelength ranges. A light collector collects multispectral images including respective images collected at each of the different wavelength ranges at which the tissue region is illuminated. A catheter positions the light source and light collector proximate the tissue region of the heart wall for respectively illuminating the tissue region and collecting the multispectral images. A display circuit collects and displays one or more images depicting a condition of the health of heart wall tissue, based on the respective images collected at the different ones of the wavelength ranges.

21 Claims, 3 Drawing Sheets

(56) References Cited

U.S. PATENT DOCUMENTS

| | | | |
|---|---|---|---|
| 5,784,162 | A | 7/1998 | Cabib et al. |
| 6,937,885 | B1 | 8/2005 | Freeman |
| 7,662,152 | B2 | 2/2010 | Sharareh et al. |
| 8,025,661 | B2 | 9/2011 | Arnold et al. |
| 8,123,745 | B2 | 2/2012 | Beeckler et al. |
| 8,147,484 | B2 | 4/2012 | Lieber et al. |
| 8,152,795 | B2 | 4/2012 | Farr et al. |
| 8,160,680 | B2 | 4/2012 | Boyden et al. |
| 8,175,688 | B2 | 5/2012 | Lewis et al. |
| 8,180,436 | B2 | 5/2012 | Boyden et al. |
| 8,241,272 | B2 | 8/2012 | Arnold et al. |
| 2006/0184037 | A1 | 8/2006 | Ince et al. |
| 2007/0024946 | A1 | 2/2007 | Panasyuk et al. |
| 2008/0058786 | A1 | 3/2008 | Boyden et al. |
| 2008/0108867 | A1 | 5/2008 | Zhou |
| 2008/0306337 | A1 | 12/2008 | Livingston et al. |
| 2009/0005768 | A1 | 1/2009 | Sharareh et al. |
| 2009/0012378 | A1 | 1/2009 | Ince |
| 2010/0168572 | A1 | 7/2010 | Sliwa et al. |
| 2011/0082451 | A1 | 4/2011 | Melsky |
| 2012/0150164 | A1 | 11/2012 | Lee et al. |
| 2014/0114304 | A1 | 4/2014 | Wang et al. |

OTHER PUBLICATIONS

Tang et al, "A Comparison of Cunyite and Fosterite NIR Tunable Laser Tissue Welding Using Native Collagen Fluorescence Imaging." 2000. Journal of Clinical Laser Medicine & Surgery; 18(3), pp. 117-123. Abstract Only.

Demos et al, "Real time assessment of RF cardiac tissue ablation with optical spectroscopy." 2008. Optics Express, Optics Express; 16(19), pp. 15286-15296.

Ahmed et al. "Initial clinical experience with a novel visualization and virtual electrode radiofrequency ablation catheter to treat atrial flutter." 2011. Heart Rhythm; 8(3), pp. 361-367. Abstract Only.

Fujimura et al, "Direct in vivo visualization of right cardiac anatomy by fiberoptic endoscopy: observation of radiofrequency-induced acute lesions around the ostium of the coronary sinus." 1994. European Heart Journal; 15(4), pp. 534-540. Abstract Only.

Eversull et al, "Direct visualization of cardiac radiofrequency ablation lesions." 2009. Journal of Cardiovascular Translational Research; 2(2), pp. 198-201. Abstract Only.

Irani et al, "Visualizing ablation gaps in vitro using a deflectable fiber optic endocardial visualization catheter." 2009. Journal of Interventional Cardiac Electrophysiology; 25(2), pp. 107-110. Abstract Only.

Schade A et al, "Pulmonary vein isolation with a novel endoscopic ablation system using laser energy." 2012. Expert Review of Cardiovascular Therapy; 10(8), pp. 995-1000.

Swartling et al, "Changes in tissue optical properties due to radio-frequency ablation of myocardium." 2003. Medical and Biological Engineering and Computing; 41(4), pp. 403-409. Abstract Only.

Wang et al, "Intraprocedural Techniques: Angioscopy and Optical Imaging." in Cardiac Imaging in Electrophysiology, Springer London, 2012, pp. 149-159. Abstract Only.

Yoshimura et al, "Relationship between damaged fraction and reflected spectra of denaturing tissues." 2005. Lasers in surgery and medicine; 37(4), pp. 308-313.

VISUALIZATION OF HEART WALL TISSUE

FIELD

Aspects of various embodiments are directed to imaging tissue such as heart wall tissue.

BACKGROUND

Imaging tissue can be useful for a variety of applications. For instance, when a physician or other medical professional is investigating internal tissue characteristics or carrying out medical procedures on internal tissue, images of the tissue can be very helpful. Many such approaches are carried out using catheters or other similar tools that assist in interacting with the tissue.

Many tissue-related procedures involve heart tissue. One such procedure involves ablation, which can be carried out to isolate electrical signals in a patient's heart. A physician performing an ablation procedure may use the tip of a catheter to selectively burn, or ablate, areas and lines of tissue. However, such an approach can be challenging as imaging the tissue for analysis of the procedure or guidance during the procedure can be insufficient. As such, there is a potential to inaccurately perform the procedure, such as inadvertently leaving gaps in desired ablation patterns/lines. Gaps in the ablation procedure can lead to a failure to stop arrhythmias. These and other procedures with heart and other types of tissue benefit from visualization and analysis/differentiation, such as for visualization of heart wall features for accurate implementation and verification of ablation procedures and determination of the health of heart tissue. However, this visualization remains challenging.

SUMMARY

Various example embodiments are directed to imaging and imaging-related apparatuses, methods and their implementation.

According to an example embodiment, an apparatus includes a light source, light collector, catheter and display circuit. The light source includes an array of light emitters that illuminate a tissue region of a heart wall with light at a plurality of different wavelength ranges. The light collector collects multispectral images, respective ones of the images being collected at each of the different wavelength ranges at which the tissue region is illuminated by the light source. The catheter operates with the light source and the light collector to position the light source and light collector proximate the tissue region of the heart wall for respectively illuminating the tissue region and collecting the multispectral images. The display circuit collects and displays at least one image depicting a condition of the health of the heart wall tissue, based on the respective images collected at the different ones of the wavelength ranges.

Another embodiment is directed to a method as follows. A tissue region of a heart wall is illuminated with light at a plurality of different wavelength ranges. Multispectral images are collected from the illuminated tissue region, with respective ones of the images being collected at each of the different wavelength ranges at which the tissue region is illuminated. One or more images depicting a condition of the health of heart wall tissue are provided, based on the respective images collected at the different ones of the wavelength ranges.

Another embodiment is directed to an apparatus that induces a fluorescent response from a tissue region of a heart wall. A light source includes an array of light emitters that induce the fluorescent response by illuminating the tissue region with light at a plurality of different wavelength ranges. A filter blocks reflected light from the tissue region, and a light collector collects images of the fluorescent response of the tissue region as the tissue region is sequentially illuminated with light at the respective wavelength ranges, in which the wavelength ranges of the fluorescent response are longer than the wavelengths of the illumination light. A catheter positions the light source and light collector proximate the tissue region of the heart wall for respectively illuminating the tissue region and collecting the fluorescent response. A display circuit collects and displays one or more images depicting a condition of the health of the heart wall tissue, based on the collected images.

The above discussion/summary is not intended to describe each embodiment or every implementation of the present disclosure. The figures and detailed description that follow also exemplify various embodiments.

DESCRIPTION OF THE FIGURES

Various example embodiments may be more completely understood in consideration of the following detailed description in connection with the accompanying drawings, in which.

Figure 1:
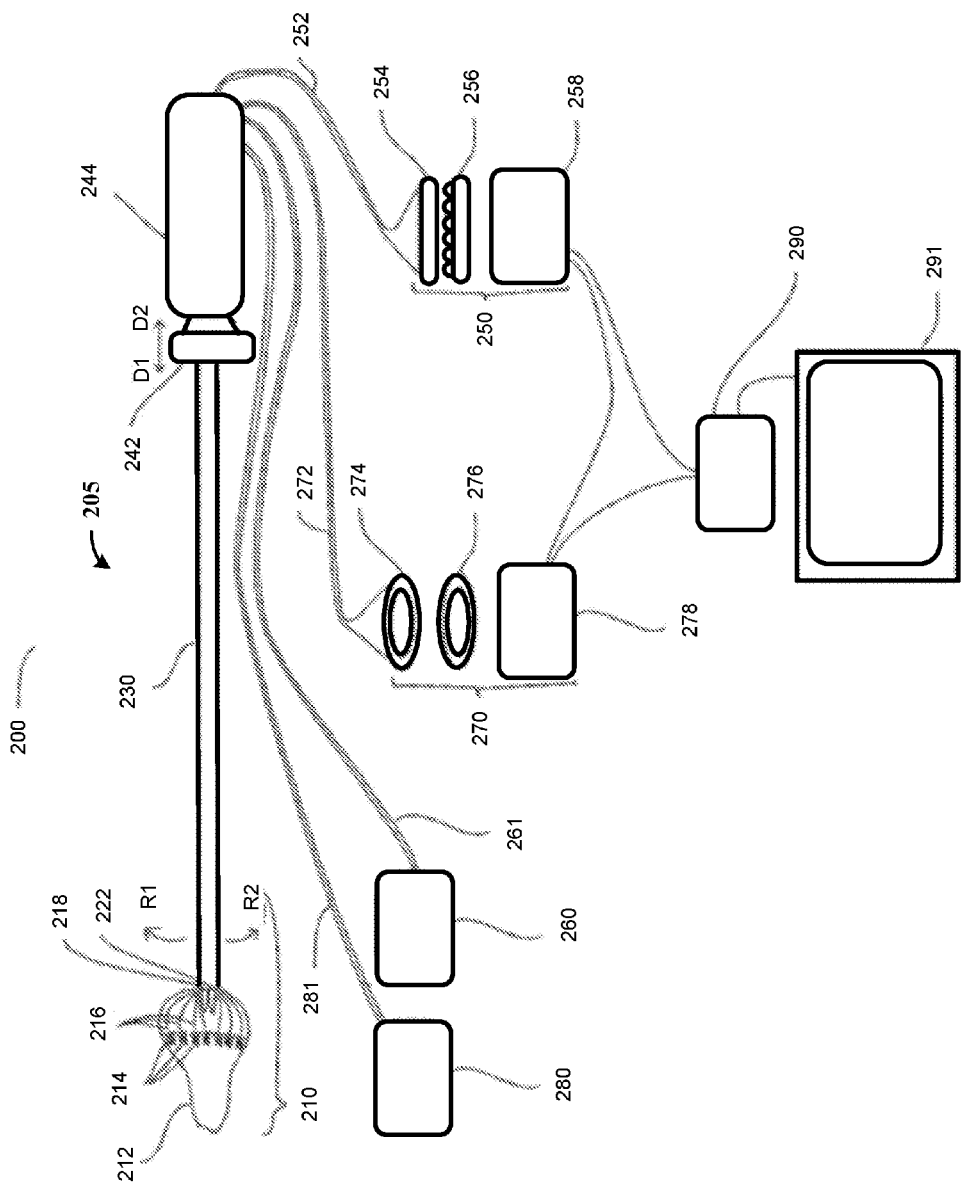
FIG. 1 shows an imaging apparatus, in accordance with one or more example embodiments.

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION

Aspects of the present disclosure are believed to be applicable to a variety of different types of apparatuses, systems and methods involving tissue imaging. While not necessarily so limited, various aspects may be appreciated through a discussion of examples using this context.

Various aspects of the present disclosure are directed toward apparatuses, devices and methods for visualizing/analyzing the state of a tissue region, such as a tissue region of a heart wall as may include ablated or scarred heart tissue, and non-ablated or non-scarred heart tissue. For instance, ablation procedures may be performed to stop arrhythmias, which may occur when regions of a heart contract at an unhealthy rate or rhythm. Certain embodiments are directed to catheter ablation procedures for atrial fibrillation (AF), to create ablation lines or lines of scar tissue that do not conduct an electrical signal. Such ablation lines can be created in a position or positions that can block arrhythmic signals from progressing through the heart, such as by creating the ablation lines such that gaps are not present.

Accordingly, various embodiments are directed to imaging tissue to ensure that an ablation process blocks arrhythmic signals, such as by imaging heart tissue to identify the location of that tissue which has been ablated, or to identify the general location of heart wall features.

In these contexts, multispectral imaging may include recording light intensities in multiple bands, which may go beyond RGB (red, green, blue) bands that cameras often use. The number of bands may be varied depending on the application and can range between as few as four to several tens of bands. In the latter case, such imaging techniques are sometimes referred to as hyperspectral imaging. These modalities measure the amount of light in a particular band that reaches the imaging sensor.

A variety of different types of tissue are imaged to suit particular embodiments. As such, various examples as discussed herein in connection with heart tissue may be implemented with other types of tissue. In accordance with various embodiments, it has been discovered that by using respective images of tissue taken under different wavelengths of illumination of the tissue, features such as ablated tissue or scar tissue (as may relate to ablation) are more readily identifiable. In certain embodiments, wavelengths of light known to reflect with higher intensity from scar tissue relative to other tissue are used to identify scar tissue.

In another example embodiment, an apparatus includes a light source having an array of light emitters that generate light at a plurality of different wavelength ranges (e.g., ultraviolet, visible, and/or infrared spectra), which may be implemented for imaging tissue. In some implementations, the emitters operate to sequentially emit light of different wavelengths or wavelength ranges, which can be used to illuminate tissue sequentially. A light collector collects multispectral images at each of the different wavelength ranges at which a tissue region is illuminated by the light source. For instance, where the emitters sequentially emit light of different wavelengths, the light collector may collect respective multispectral images from the tissue as it is illuminated at each of the different wavelengths. A catheter positions the light source and light collector proximate the tissue region of the heart wall for respectively illuminating the tissue region and collecting the multispectral images. In some embodiments, the catheter includes additional components that facilitate interaction with the tissue, such as to ablate heart tissue as discussed above. A display circuit collects and displays one or more images depicting a condition of the health of heart wall tissue, based on the respective images collected at the different ones of the wavelength ranges. Such approaches can be used with a variety of different types of tissue.

In certain embodiments, intensity of the collected light is used to facilitate the detection of characteristics of the tissue. In some implementations, the collected light is used to generate an image that depicts a condition of the health of heart wall tissue, by combining intensities of ones of the respective images. The resulting image visually distinguishes scarred tissue from unscarred tissue, or visually distinguishes ablated tissue from tissue that is not ablated, via the combined intensities (e.g., where scarred or ablated tissue provides increased reflectance). For instance, where scarred or ablated tissue is known to reflect a certain wavelength of light with greater intensity relative to other wavelengths of light, such knowledge can be used with the combination to provide an image that more readily identifies the scarred/ablated tissue.

Accordingly, some embodiments involve illuminating regions of tissue with wavelengths of light that reflect from scar tissue or ablated tissue with a higher intensity relative to unscarred or non-ablated tissue. In certain embodiments, a display circuit or other computing device uses the intensity of reflected light that forms the multispectral images to provide an indication of the presence of scarred tissue, based on an expected intensity of light to be reflected from unscarred tissue at the respective wavelengths and the detected intensity of the reflected light. As such, the intensity itself can be used as an indication of the type of tissue from which the light reflects. These and other approaches may, for example, be used in identifying a region of interest in images of tissue such as heart wall tissue, and displaying an image that visually distinguishes scar tissue from unscarred tissue by combining intensities of the region of interest from a plurality of the respective images. In certain embodiments, intensities of the region of interest are added as depicted in the plurality of respective images, and intensities of regions of the plurality of respective images that do not include the region of interest are subtracted.

The different wavelengths of illumination light are provided and implemented in a variety of manners. In some embodiments, the light source illuminates the tissue region with pulses of light, with each pulse being of light having one of the plurality of different wavelengths. The light collector operates in conjunction with the light source to collect each of the multispectral images. For instance, an image of the tissue region can be collected as illuminated with each pulse of light. This imaging can be carried out sequentially for each pulse, with respective frames of an image corresponding to a specific wavelength of light. In some implementations, a display or computer circuit provides an image depicting a condition of the health of the heart wall tissue by combining portions of the respective images obtained for each such pulse of light.

In certain embodiments, the above-discussed apparatus also includes an ablation device that ablates portions of the heart wall while the light source, light collector and catheter operate to illuminate and collect the respective images from the heart wall. The ablation device thereby provides an indication of the portions of the heart wall having been subjected to ablation. This approach can be used, for example, to guide ablation or image tissue after ablation.

In a more particular embodiment, the light source effects a fluorescent light response from the tissue region by illuminating the tissue region with light that stimulates the tissue region to generate the fluorescent light. The light collector collects both reflected light from the tissue region and the fluorescent light emitted by the tissue region, which are displayed (e.g., via the catheter and display circuit) in at least one image that is based on both the reflected light and the fluorescent light. Fluorescence imaging in this regard provides information about the tissue that is distinct from surface spectral reflectance. Such fluorescence may occur when a chemical group is excited by light of a particular range of wavelengths. In general, a fluorescent chemical group is predisposed to absorb energy at a range excitation wavelengths. After excitation, the chemical group returns to its ground state. In the process, it emits light that is of a characteristic emission wavelengths.

Various embodiments are directed to method-based implementations, such as methods that may be implemented using one or more apparatus-based aspects as noted above. In some embodiments, such a method includes illuminating a tissue region of a heart wall with light at a plurality of different wavelength ranges, and collecting a plurality of multispectral images including respective images collected at each of the different wavelength ranges at which the tissue region is illuminated. One or more images depicting a condition of the health of heart wall tissue are collected and displayed, based on the respective images collected at the different ones of the wavelength ranges. Such an approach can be implemented with a catheter proximate tissue region of the heart wall for respectively illuminating the tissue region and collecting the multispectral images.

The images are collected and displayed in a variety of manners. In some embodiments, an image is provided which depicts a condition of the health of heart wall tissue by combining intensities of ones of the respective images and displaying an image that visually distinguishes scarred tissue from unscarred tissue, or that visually distinguishes ablated tissue from tissue that is not ablated, via the combined intensities. In certain embodiments, one or more regions of interest are identified in one of the respective images, and intensities of light reflected from the region of interest as depicted in the plurality of respective images are added, while intensities of regions of the plurality of respective images that do not include the region of interest are subtracted.

Tissue can be illuminated in a variety of manners, to suit particular embodiments. In some embodiments, a tissue region as above is illuminated with pulses of light, each pulse being of one of the plurality of different wavelengths. For each of the pulses of light, a multispectral image of the tissue region is collected, as illuminated with the pulse of light. In some embodiments, portions of respective images obtained for each pulse of light are collected and displayed as combined. In certain implementations, the tissue region is illuminated with light having a wavelength that reflects from scar tissue with a higher intensity relative to unscarred tissue, relative to an intensity of other wavelengths of light that reflect from the scar tissue. The higher intensity of the light reflecting from the scar tissue is used to identify the scar tissue in the image.

In further implementations, a fluorescent light response is induced from tissue region by illuminating the tissue region with light that stimulates the tissue region to generate the fluorescent response. The fluorescent light emitted by the tissue region is collected (e.g., with or without reflected light), and an image is generated and displayed based on the collected light. For instance, by exciting heart tissue using light in the 335-365 nm range, the heart tissue emits light at a range of wavelengths centered at 460 nm. In connection with these embodiments, it has been recognized/discovered that changes in emissions can be attributed to changes in metabolic activity in the heart tissue, which may be terminated via ablation. These metabolic changes may affect a reduction in a molecule called NADH (nicotinamide adenine dinucleotide), which effects auto-fluorescence. Accordingly, auto-fluorescence due to NADH can be markedly reduced in areas having been ablated, and this can be used to identify those ablated areas as those exhibiting decreased NADH auto-fluorescence. In various aspects, multi-spectral fluorescence is used, in which the tissue is excited with different colors of light. Different ranges of the fluorescence spectrum are imaged (e.g., using the same camera, at almost the same time). For each excitation light, emitted light can be collected at several wavelengths. It has been recognized/discovered that heart tissue displays a detectable increase in auto-fluorescence at many bands in the visible range when it is excited with blue, green, or yellow light. These ranges may relate to chemical groups that are different from NADH, as discussed herein (e.g., such as nicotinamide adenine dinucleotide phosphate-oxidase (NADPH) and collagen, with collagen loss during ablation or increases due to scar formation). Moreover, various stimulation approaches achieve auto-fluorescence without using UV light (and can thus avoid issues that may arise with using UV light).

Certain aspects of the present disclosure are directed toward apparatuses or methods as exemplified or supported by aspects of the above noted description/embodiments, as well as the description/embodiments of the appendices filed as part of the underlying provisional application. For instance, certain embodiments of the present disclosure are directed to use of an assembly that collects fluorescent images or multispectral images of heart wall tissue. The assembly includes at least one light source having an array of light emitters that illuminate a tissue region of the heart wall with light in one or more wavelength ranges. The light source can illuminate the tissue region at one or more wavelength ranges in the ultraviolet, visible, and infrared ranges. For example, the light source may illuminate the tissue at wavelength ranges of 325-375 nm and 445-490 nm for collection of the fluorescent images. Additionally, the light source can also illuminate the tissue with light in wavelength ranges for the collection of multispectral imaging. For example, the light source can illuminate at several wavelength ranges between 450-550 nm and between 590-750 nm for collection of the multispectral images. These wavelength ranges may be divided into smaller wavelength ranges, for example wavelength ranges of 450-500 nm, 590-650 nm, 650-700 nm, and 700-750 nm. In some embodiments, the light emitters in the array each provide illumination at one of the wavelength ranges.

In some embodiments, a light assembly includes a light collector that collects fluorescent and/or multispectral images. The fluorescent images are collected from fluorescent light, which has a wavelength range that is longer than the wavelength range of the illumination light. For example, during illumination with the 325-375 nm wavelength range, fluorescent light may be collected at wavelengths longer than 400 nm. Similarly, during illumination in the 445-490 nm wavelength range, fluorescent light at wavelengths longer than 500 nm may be collected. However, illumination of the tissue in these wavelength ranges produces reflected and fluorescent light. Reflected light has the same wavelength range as the illumination light, and generally has a greater intensity than fluorescent light. To collect fluorescent light, reflected light may be blocked from reaching the light collector by using a filter. For example, when illuminating in the 325-375 nm wavelength range, a filter blocking light with a wavelength shorter than 400 nm may be placed in front of the light collector, so that only fluorescent light reaches the light collector. Similarly, when illuminating in the 445-490 nm wavelength range, a filter blocking light with a wavelength range shorter than 500 nm may be placed in front of the light collector to selectively image fluorescent light and block reflected light.

Multispectral images may be collected from reflected light, in certain embodiments without using a filter. For example, a multispectral image sequence may be collected by sequentially illuminating the tissue region with wavelength ranges of 450-500 nm, 590-650 nm, 650-700 nm, and 700-750 nm, and collecting an image during the illumination with light from each wavelength range. In certain embodiments, multispectral images consisting primarily of reflected light are collected without placing a filter in front of the light collector, because the intensity of the reflected light is substantially greater than the intensity of fluorescent light. As may be implemented here and/or with other embodiments, a multispectral image sequence is also called a multispectral image cube.

In certain embodiments, both multispectral and fluorescent images are collected. For example, the light collector may contain a filter that blocks light below 400 nm. The light source may sequentially illuminate the tissue with light in the five wavelength ranges of 325-375 nm, 450-500 nm, 590-650 nm, 650-700 nm, and 700-750 nm. The light collector may be synchronized with the light source such that an image is collected by the light collector as the tissue is illuminated with light from each of these five wavelength ranges. In this configuration, the assembly produces a fluorescence image corresponding to illumination in the wavelength range of 325-375 nm, and a multispectral image sequence that consists of four images corresponding to the illumination ranges of 450-500 nm, 590-650 nm, 650-700 nm, and 700-750 nm.

In certain other embodiments, both multispectral and fluorescent images are collected by the assembly, by using a dynamic filter in the light collector. The dynamic filter is a filter that may be changed such that the light is filtered at times and not filtered at other times. Changing of the filter may occur by moving one or more filters into and out of the path of the light. Changing of the filter may also be effected by using a filter that is not moved, but has optical filtration properties that can be adjusted with an electronic signal. For example, a liquid crystal tunable filter or an acousto-optic tunable filter may be used as the dynamic filter. One embodiment with the dynamic filter includes two movable filters that can be positioned such that the light reaching the light collector is either not filtered, or filtered to block light below 400 nm, or filtered to block light below 500 nm. The light source of such an embodiment would sequentially illuminate the tissue with light in the six wavelength ranges of 325-375 nm, 445-490 nm, 450-500 nm, 590-650 nm, 650-700 nm, and 700-750 nm. The light collector collects an image of the tissue as it is illuminated with each of the six wavelength ranges. As the light is illuminated with 325-375 nm and 445-490 nm wavelength ranges, filters are positioned such that light wavelengths less than 400 or 500 nm, respectively, are blocked from reaching the light collector. For the remaining four illumination wavelength ranges, the light reaching the light collector is not filtered. In this embodiment, the assembly produces two fluorescence images corresponding to illumination in the wavelength range of 325-375 nm and 445-490 nm, and a multispectral image sequence that consists of four images corresponding to the illumination ranges of 450-500 nm, 590-650 nm, 650-700 nm, and 700-750 nm.

In certain embodiments, the light source and light collector are synchronized to produce image sequences at a video rate of 15 or more images each second. In one implementation, the light source illuminates the tissue sequentially at five wavelength ranges of 325-375 nm, 450-500 nm, 590-650 nm, 650-700 nm, and 700-750 nm. The light source may cycle through the five wavelength ranges so that illumination with each wavelength range lasts for an 8 millisecond duration. The filter may block light below 400 nm. The light collector may be synchronized with the light source to collect an image of the tissue under the illumination of each wavelength range. Such an embodiment may, for example, collect 125 images each second, with 25 images each second corresponding to each illumination wavelength, and produce an image sequence at a video rate of the fluorescent images and multispectral images.

Fluorescent and/or multispectral images as collected herein are visualized, for example to a physician, using a display. In certain embodiments, the images may be visualized as an image sequence at video rates.

Various apparatuses and/or assemblies as consistent with various aspects of the present disclosure include a steerable imaging sheath that positions a light source, light collector, and an ablation catheter as discussed herein, at a tissue region of interest (e.g., a heart wall). The sheath may contain a lumen appropriately sized to fit the ablation catheter. Thus an ablation catheter may be passed through the sheath and brought into contact with the heart wall, in a region similar to the region that is imaged by the light collector. The end of the sheath may be steerable to adjust the position of the light source, light collector, and ablation catheter. Steering of the sheath may be achieved using a mechanism of pull wires. The assembly may also include a balloon that is used to clear blood from the field of view so that clear images may be obtained. In such an embodiment, the assembly may be used to display multispectral and/or fluorescent images and video of the region of heart wall tissue, before, during, and after the tissue is ablated with the ablation catheter.

In certain more specific embodiments of the present disclosure, the visualization of the fluorescent images or the multispectral images includes distinguishing between ablated and non-ablated regions of heart wall tissue. The visualization may include comparing fluorescent and/or multispectral images in ablated and non-ablated regions, or comparing images of a region before an ablation is applied to images of the same region during or after an ablation is applied. For example, when illuminated at 325-375 nm and visualized at wavelengths greater than 400 nm, a relative decrease in fluorescence may correspond to ablation of the tissue. When fluorescence images are illuminated at 445-490 nm, and visualized at wavelengths greater than 500 nm, an increase in fluorescence may correspond to a mild ablation, and a loss of fluorescence may correspond to a more extensive ablation. When a multispectral image is recorded by illuminating the tissue in the range of 500 nm, an increase in reflectances may indicate that ablation has occurred. Fluorescent and multispectral images may also be mathematically combined and compared to indicate an ablation. For example, an image representing the reflectance in the range of 590 to 650 nm maybe subtracted from an image representing the reflectance in the range of 700 to 750 nm, generating a differential image representing the difference of the reflectance in these wavelength ranges. Regions in the differential image with greater reflectance differences may indicate the presence of an ablation. Further, the visualization of the fluorescent images or the multispectral images can include thresholding the image or images to characterize features of heart wall tissue by categorizing the images using one or more of the following methods: histogram-shape based, entropy-based, cluster-based, object-attribute based, local and spatial thresholding. In certain embodiment, various apparatuses and methods of the present disclosure involve an ablation arrangement that applies electrical impulses to ablate heart tissue.

As noted above, a variety of types of tissue and related medical conditions can be analyzed, and a variety of imaging applications can be implemented, using approaches as described herein. For instance, conditions related to endocardial tissue, such as interstitial edema, fibrosis, endocarditis, hypertrophy, cell death and infarct regions can be imaged. In particular, the level of and pattern of fibrosis in the left atrium of the heart may provide diagnostic information that helps guide the treatment of atrial fibrillation. The collection of this data may also be useful to diagnose and evaluate infections in the heart, cardiac hypertrophy, heart failure, and myocardial infarction.

In another embodiment, tissue is imaged for lead placement, sensor placement, and drug delivery. In some implementations, the quality of a site within an organ such as the heart can be evaluated for the placement of a lead or sensor. Such devices include pacemakers, leadless pacemakers, intra-cardiac ECG devices, implantable cardioverter defibrillators, and intra-cardiac pressure sensors. Many of these types of devices are physically anchored into the heart wall, for example with a screw. In regions were the tissue is unhealthy, it is difficult to attach the anchor securely. It may not attach at all, or come loose over time. Thus, an assessment of the tissue health with the proposed imaging system may help identify desirable positioning.

In various embodiments involving drug delivery, substances including traditional pharmaceuticals, biologics, biomaterials, and cell therapies can be injected into the heart wall. Often, it is desirable to inject the drug in a specific location relative to a myocardial infarct or region of fibrosis. Imaging approaches as discussed herein can be used to identify such a location for the injection by identifying areas of scarring.

Various approaches are used to identify ablated or scarred tissue. In some machine-vision type approaches, images of a small set of test ablations are collected at the beginning of a medical procedure. This dataset, in conjunction with a global database, is used to train a classifier (algorithm) tuned to a particular patient undergoing the procedure. Alternatively, a classifier based upon a global database without patient-specific training data could also be used. Such approaches can facilitate an increase in the predictive performance of the method and the overall success of the procedure. In particular, support vector machines (SVM), linear discriminate analysis (LDA), naïve Bayes (NB), logistic regression (LRM), quadratic discriminate analysis (QDA), decision trees, and k-nearest neighbor (KNN) algorithms can be used to classify the data, and to discriminate ablation regions using both multi-spectral and fluorescent data.

The aspects of the present disclosure, as directed toward apparatuses, devices, and methods, can be utilized alone or in combination with various other aspects. Although specific wavelength ranges are discussed here, other ranges may be included, in addition to or instead of the wavelength ranges discussed here.

For information regarding details of other embodiments, experiments and applications that can be combined in varying degrees with the teachings herein, reference may be made to the experimental teachings and underlying references provided in the appendices which form part of the underlying provisional application, and which are fully incorporated herein by reference. Embodiments discussed in these appendices are not intended, in any way, to be limiting to the overall technical disclosure, or to any part of the claimed disclosure unless specifically noted. These documents were identified as Appendices A and B. Appendix B provided a further description of various aspects of Appendix A including, for example, FIG. 3 and its related discussion.

Turning now to the figures, FIG. 1 shows an imaging apparatus 200, in accordance with one or more example embodiments. The apparatus 200 may be used to obtain fluorescent or multispectral images to visualize the state of health of tissues in the heart wall. The apparatus 200 includes a catheter 205 that is connected to a light source and a light collector, which is in turn connected to a display circuit. Although specific numbers of LEDs, illumination colors, and frame rates, are described here, this and other embodiments of the invention are not limited to these values.

The catheter 205 may take various forms, and is shown here having a distal end 210, with a balloon, 212, a plurality of ablation electrodes 214, wires 216, an imaging lens 218, and an illumination lens 220. Wires 216 are electrically connected to the electrodes 214, which may be fastened to the surface of balloon 212. The electrodes 214 may be thin or flexible so they can expand and contract with the surface of balloon 212 when it is inflated or collapsed. End 210 is mechanically connected to a flexible shaft 230, which is connected to a handle 244 having a slidable steering knob 242.

The catheter 205 is connected to a light source and a light collector, which is in turn connected to a display circuit. In some embodiments (as shown), handle 244 is connected by fiber optics to a light source unit 250, by fiber optics to imaging unit 270. Optionally, handle 244 is also connected via one or both of a conductive wire to a radiofrequency generator 260, and tubing to a pump system 280, which may be respectively use to provide power (e.g., for ablation) and fluid delivery and/or other light sources, imaging units (light collectors), energy generators and fluid systems may be used to suit particular embodiments.

As shown, light source unit 250 includes a fiber optic cable 252, a lens, 254, an array of a plurality of light emitting diodes (LEDs) 256, and a microprocessor 258. Imaging unit 270 includes a fiber optic cable 272, a longpass optical filter 274, an optical liquid-crystal tunable filter 276, and a charge-coupled device camera 278. Camera 278 and microprocessor 258 are connected by wires to a computer 290, which is connected by a cable to a display monitor 291. In the context of various embodiments, a display circuit refers to a computer 290 that operates to provide an output that can be displayed on a variety of displays, such as display monitor 291.

Figure 2:
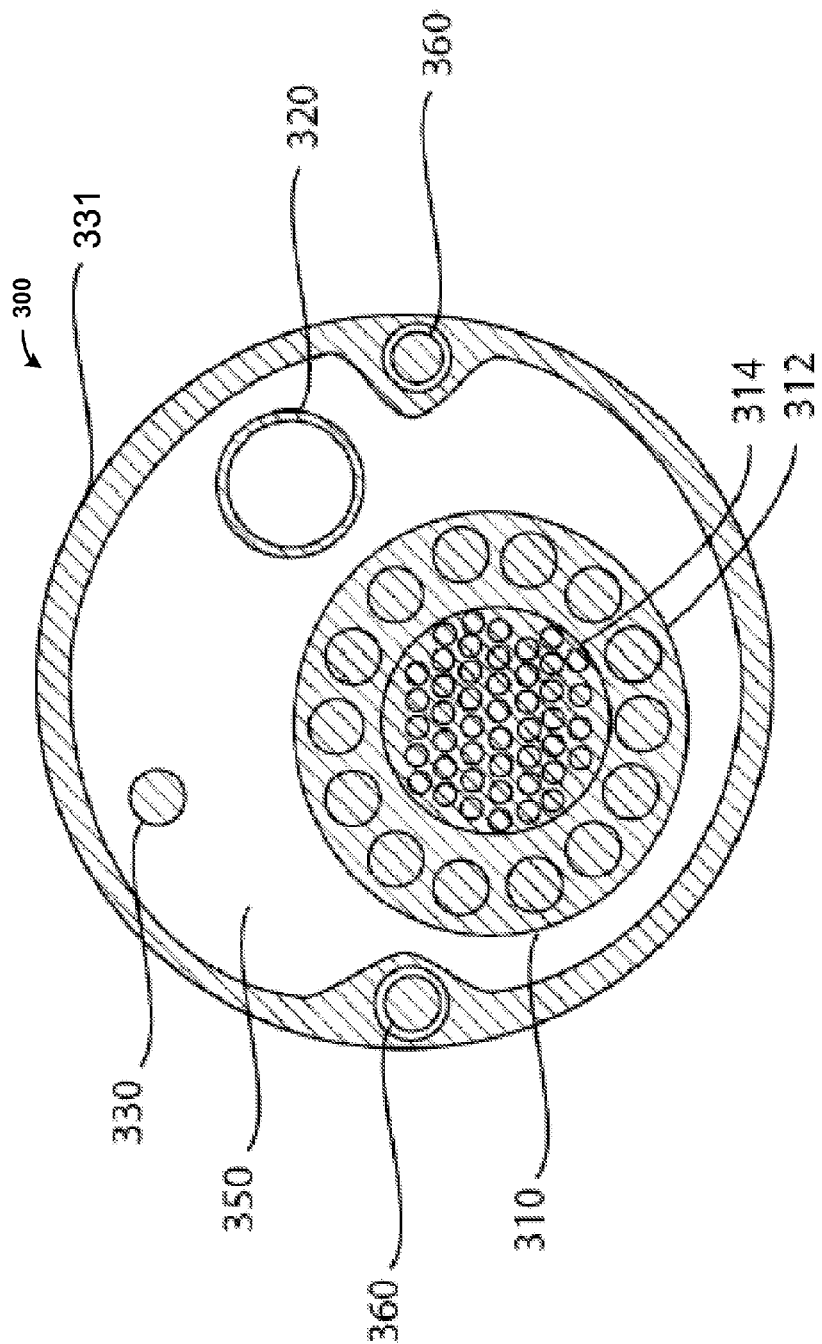
FIG. 2 shows a cross-sectional view of an imaging apparatus, in accordance with another example embodiment.

FIG. 2 shows a cross-sectional view of an imaging apparatus 300, in accordance with another example embodiment. The apparatus 300 may, for example, be implemented within shaft 230 of FIG. 1, as represented by lumen 331 in FIG. 2. The following discussion reflects such an application, with the understanding that the apparatus 300 may be used with a variety of different catheter-type approaches.

Lumen 331 includes an open lumen 350. Running through the lumen, and also shown in cross-section, are steering wires 360, radiofrequency wire 261, fiber optic cable 310, and fluid tube 320. Running through cable 310 is a ring of illumination fiber optics 312 and a core of visualization fiber optics 314. Wires 360 may be mechanically connected to knob 242, and end 210 (shown in FIG. 1) so that sliding of knob 242 in direction D1 or D2 alternatively places tension on either of wires 360. This tension generates curving of shaft 230 in directions R1 or R2. Such curving or steering of shaft 230 is desirable for a physician to guide end 210 into a desired position. Radiofrequency wire 330 may be electrically connected to wires 216 at the end 210, and to radiofrequency generator 260. Generator 260 may also be connected to electrode pads that may be connected to a patient receiving treatment with the apparatus 200. Generator 260 can be used to apply radiofrequency energy to tissue in contact with electrodes 214. Fiber optics 312 may be connected optically with illumination lens 220 at end 210, and with cable 252, at the proximal end of the catheter.

Through these connections, light generated by light source 250 travels to the distal end 210 and may pass through balloon 212 to illuminate and reflect off of surrounding tissues. The LEDs of array 256 are positioned to project illumination through lens 254. Array 256 is connected to and controlled by microprocessor 258, which is further connected to computer 290. Each individual LED in array 256 may produce light at different range of wavelengths. Thus, computer 290 can signal a predetermined sequence of activation of individual LEDs in array 256 such that tissue near balloon 212 is exposed to the colors of light generated by the LEDs at a predetermined rate and sequence. Microprocessor 258 may also be connected to camera 278, such that the flashing of LED array 256 may be synchronized with the collection of images with camera 278.

Fiber optics 314 are in optical communication with imaging lens 218 at end 210 and to cable 272 at the proximal end, such that a light from of the inside of the balloon may be passed through longpass filter 274, liquid crystal tunable filter 276, to camera 278. This system may be coherent so that the light passing through lens 218 is processed into an image by the sensor of camera 278. Camera 278 may transfer images created by this light to computer 290.

The walls of balloon 212 may be made from a transparent material, so that light frequencies of interest (e.g., as discussed below) can pass through the balloon. Fluid tube 281 is connected to the inside of balloon 212 and pump 280, so that pump 280 may apply pressure and vacuum to respectively inflate and deflate balloon 212. Balloon 212 may have a tapered shape, be made of a compliant material, and be sized such that when inflated in the ostium of the pulmonary vein, it expands to fill the non-circular area of the ostium and substantially contacts the ostium around its circumference.

In some embodiments, an apparatus 200 constructed as shown in both FIG. 1 and FIG. 2 can be inserted into a patient's artery or vein with end 210 guided into the ostium of a pulmonary vein, similar to atrial fibrillation ablation procedures commonly performed by physicians. Apparatus 200 can further be used to inflate the balloon 212 in the ostium of the pulmonary vein, and substantially occlude the vein ostium. Apparatus 200 can further illuminate the heart wall with a wide variety of colors of light, generated by the LEDs of array 256, and a wide range of sequences and patterns of illumination. Apparatus 200 may also acquire images and videos of the tissue under different colors and sequences of illumination.

Figure 3:
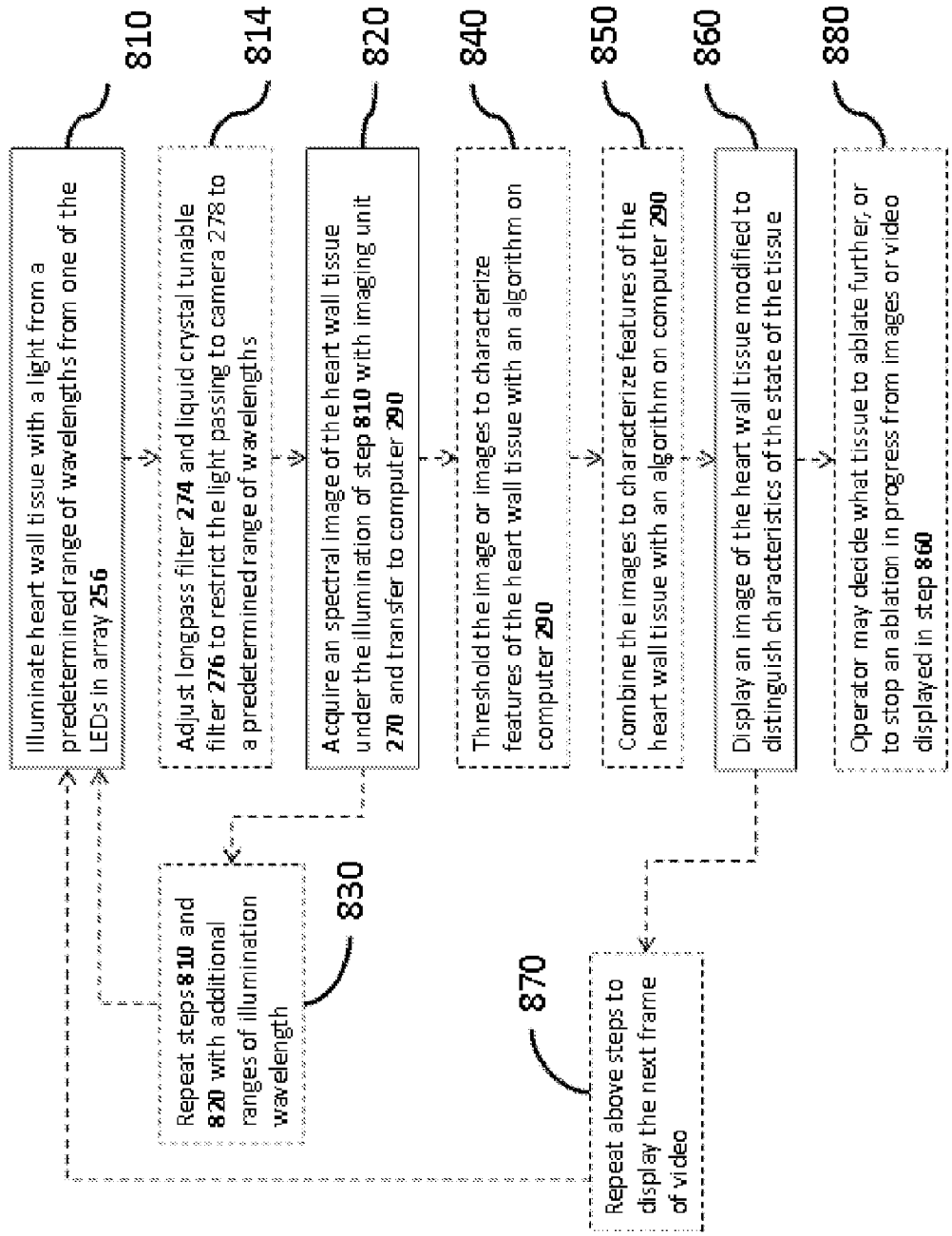
FIG. 3 shows a method for providing multispectral images of tissue, in accordance with another example embodiment.

FIG. 3 shows a method for providing multispectral images if tissue, in accordance with another example embodiment. The approach shown in FIG. 3 may, for example, be implemented with aspects as depicted in one or both of FIGS. 1 and 2. In this context, the following discusses embodiments as may be implemented in the context of FIG. 1 and/or FIG. 2, with the understanding that the various steps as shown may be implemented in a variety of manners, to suit particular embodiments.

In step 810, light from the LED of array 256 can be projected through balloon 212 to illuminate the tissue in a predetermined color of light. As an example, array 256 may contain seven LEDs capable of flashing light at a frequency of approximately 140 Hz. LEDs of array 256 may be selected to produce light in the ranges of 350 to 400 nm, 400 to 450 nm, 450 to 500 nm, 500 to 600 nm, 600 to 700 nm, 700 to 800 nm, and 800 to 900 nm. In step 820, imaging unit 270 acquires an image of the tissue under the predetermined illumination. Once the image is collected it may be transferred to computer 290.

As noted in optional step 830, steps 810 and 820 may be repeated, for example to take an image under the illumination of each color of light from the LED array 256. For instance, camera 278 may be synchronized with LEDs flashing to collect 140 image frames per second, with each frame collected as the tissue is exposed to a flash of LED illumination. The sequence of illumination may cycle repeatedly through all seven LED colors so that 20 image frames per second are taken with each illumination color.

In step 840, the images may be thresholded to remove noise and otherwise distinguish features of interest. In step 850, the images from the different sources of illumination may be combined to best distinguish features of interest. For example, the intensity of reflected light detected to create each pixel of the image may be added, subtracted, or otherwise combined with the corresponding pixel location of the other images to generate a final image that best distinguishes the features of interest. Because 20 frames of each color are collected per second, in this example 20 combined frames can be produced per second.

Proceeding to step 860, the image is displayed to a physician or technician involved with the operation of apparatus 200. To communicate the fluorescent and/or multispectral data to the operator of apparatus 200, multispectral data is mapped into a standard color space, such as the red-green-blue (RGB) format. Pixels representing features of interest, as determined by one or both of steps 840 and 850, may be displayed to the operator in a bright, distinguishable color in RGB color space. Alternatively, borders may be drawn around features of interest to highlight the feature location and geometry to the operator.

As noted above, in step 870, steps 810 through 860 may be repeated continuously to display a multispectral video of the tissue surface. In step 880, the physician may make a decision regarding the ablation procedure based on the information presented in the display. For example, the display may highlight areas of heart wall tissue that are insufficiently ablated, and the physician may decide to ablate these areas.

In some embodiments, the steps of the method in FIG. 3 are carried out while tissue is being ablated, to monitor the progress of the ablation. The display may thus distinguish areas of potential tissue damage during an ablation procedure, indicating when enough ablation energy has been applied to the tissue, when an unstable amount of steam has developed in the tissue, or when char formation is likely to begin.

In a more particular embodiment, an amount of ablation or degree of progression of ablation is determined using a combination of fluorescence and reflectance. In some implementations, a learning approach involves ablating tissue to a known time or a known amount of ablation, imaging the tissue at the known time or after the known amount of ablation has occurred, and recording the images as reference values. The reference values can then be used in estimating an amount of ablation or progression of ablation. Images can be taken, for example, in a reflectance imaging system and/or multispectral fluorescence imaging system.

In some implementations, acquired images are used in a machine-learning type analysis of image data, which can be used to determine whether an algorithm can classify between images of ablated and unablated tissue. Such an approach may involve binary classification between no ablation or low ablation, and higher ablation amounts, in which the respective classes (no/low vs. high) may have uneven numbers of samples. False versus true positives can be characterized via a receiver operator curve (ROC), or area under the ROC curve (AUC). In other implementations an indication of a degree of ablation is achieved by determining whether an algorithm can distinguish between respective levels (e.g., five different amounts of time), which may implement a confusion matrix with an equal or nearly equal number of samples. A variety of linear (e.g., support vector machine (SVM), Linear Discriminant Analysis (LDA), Naïve Bayes (NB), or Logistic Regression (MLR)), $2^{nd}$ order (e.g., Quadratic Discriminant Analysis (QDA)) and nonlinear (Trees, K-Nearest Neighbors (KNN)) algorithms are implemented to suit particular embodiments. Further, these approaches may involve reflectance, fluorescence, or both, and may be implemented based on the particular application (e.g., with reflectance providing desirable acquisition speed, fluorescence providing desirable performance (particularly in the blue channel), and with linear models that provide a balance between robustness and accuracy).

Fluorescent images and videos may be acquired with the process as shown in FIG. 3, with optional step 814 in which wavelengths of light that reach camera 278 are restricted by filters 274 and 276. Such combinations of longpass and liquid crystal tunable filters that restrict light to narrow ranges off wavelengths. For example, some components of heart wall tissue of interest are known to fluoresce when excited by light in the range of 350 to 400 nm. These components emit light in the range of 400 to 450 nm. To detect these components, the tissue could be illuminated with an LED in the range of 350 to 400 nm in step 810, and the emitted light collected by the imaging system is filtered such that only light in the range of 400 to 450 nm reaches the camera 278 in step 814. In this way, system 200 can be used to collect fluorescent images. Following the steps as discussed above, fluorescent images and videos of the tissue may be displayed to a physician operating the system and used to provide information about the health of the tissue and otherwise make decisions regarding the ablation of the heart tissue as described above.

As described above, images or videos of the fluorescence of the heart wall can be produced with apparatus 200 that algorithmically combine the images collected with different fluorescent parameters. For example, heart wall tissue may be exited with light in the range of 350 nm, and separate videos images of the emitted light in the ranges of 260 nm and 460 nm to represent collagen and NADH signals, respectively. Apparatus 200 may then display a video of processed image frames that represents the sum, difference, or ratio of these two signals, to better describe the state of health of heart wall tissue.

The state of heart wall tissue may also be visualized with an embodiment using spectral tissue properties instead of, or in addition to, fluorescent properties. As described above, apparatus 200 may be used to collect spectral images by illuminating of the heart wall tissue with a wide range of light wavelengths, spanning the ultraviolet, visible, and infrared spectra. Alternatively, the heart wall tissue may be illuminated with white light, and the reflected light may be filtered to the desired wavelengths with filters 274 and 276. In particular, deoxyhemoglobin and deoxymyoglobin may tend to scatted light in the range of 760 nm, oxyhemoglobin and oxymyoglobin may tend to scatter light in the range of 920 nm. Ablation may tend to transform these species to methemoglobin and metmyoblobin, which have significantly different absorbance and scattering spectra in the range of 500 to 700 nm. Thus, multispectral imaging in these ranges may be used to more clearly distinguish changes related to these molecular species.

The state of heart wall tissue may also be visualized with an embodiment using the principles of multi-photon microscopy and second harmonic generation. This embodiment typically employs laser illumination in the range of 800 to 2000 nm in place of array 256, as well as additional modifications. Such illumination may penetrate deep into the tissue of the heart wall to provide visualization of the state the health of the tissue.

Although the above details provide a description of some embodiments of the invention, several others are possible. For example, the tissue may be illuminated with laser light instead of LEDs. The camera and LEDs may be positioned at the distal end of the catheter system, near or within the balloon, instead of in separate illumination and imaging units with fiber optic connections. Although a CCD camera is described, a CMOS or other camera type may be used in some embodiments. The arrangement of fiber optics in FIG. 2, with visualization fiber optics 314 surrounded by illumination fiber optics 312, may be altered to other fiber optic configuration. In some embodiments, an LED located in end 210 may provide illumination instead of fiber optics 312. The system may be used with or without an ablation functionality. As an example of an embodiment without an ablation functionality, an assembly similar to apparatus 200 could be constructed without ablation electrodes 214 on balloon 212. Alternatively, the ablation functionality may apply laser, focused ultrasound, freezing, microwave, or other energy instead of radiofrequency. Instead of ablation lesions, injured tissue from myocardial infarctions, infections, or other diseases may be visualized. In various embodiments, the system collects only fluorescent images, only multispectral images, or images of both types. A cooling flush of saline could be added to prevent overheating during ablation or imaging. Or, the system may be used to identify other tissue structures within the heart. Blood may be cleared from the field of view using a flush of saline instead of balloon 212. Blood may be cleared from the field of view by pressing a transparent window, of plastic or glass, against the heart wall. The videos may be recorded and processed in a different order from the steps in FIG. 3. For example, all image frames may be recorded to memory without thresholding or other processing, and then processed subsequently. The image frames may be recorded into a memory buffer rather than transferred immediately to the computer 290. These and other variations and embodiments are possible, and included within the scope of the invention.

Various image processing algorithms are implemented to suit particular embodiments, for characterizing tissue. In some embodiments, one or more algorithms are implemented for processing the images in steps 840 and 850 of FIG. 3 as follows. In step 840, histogram-shape based, entropy-based, cluster-based, object-attribute based, local and spatial methods may be used to locate regions of interest on the tissue surface. The region may represent an area that has, or has not, been ablated. Alternatively, the thresholding may provide information about the degree of ablation, or another aspect of the tissue.

Consistent with one or more embodiments it has been discovered that reflectance increases in the range of 460 to 540 nm can be observed as tissue is ablated. Accordingly, in some embodiments tissue is illuminated at 810 with light in the range of 460 to 540 nm. Next, a grayscale image is acquired in step 820, and thresholding is performed in step 840 to segment areas with higher reflectance that may represent ablated tissue. For purposes of display, pixels that are thresholded, and thus recognized as ablated, could be assigned a false color and combined with the original grayscale image in step 850. This image is then displayed to the user in step 860, so that an image depicting the heart wall, with added color in potentially ablated areas, would be displayed.

In some embodiments, tissue is illuminated with blue light (445-490 nm) at block 810 over a broad range (about 510 to 700 nm), with high intensity around 580 nm. Then in step 814, a band pass filter is placed in front of camera 278 to prevent light below about 500 nm and above about 600 nm from reaching the image sensor of camera 278. Proceeding to step 820, an image of the fluorescence in this range is acquired. This image can be thresholded, overlaid with a grayscale reflectance image of the tissue, and displayed to the physician as described above.

In some embodiments, thresholding is carried out using a calibrated cut-off value. In other embodiments, reflectance is used rather simply segmenting out areas of relatively high reflectance. For calibrated measurement of the reflectance, an image sensor is calibrated in step 810, prior to illuminating the heart wall tissue. For instance, before inserting the instrument into the patient, the end 210 can be held close to a white standard surface of known, uniform reflectance. A box or other device could be used to shield the calibration procedure from ambient light. The LEDs in array 256 can be sequentially illuminated and images corresponding to each illumination band would be acquired. These calibration images can be saved for reference. In step 840, the pixel values of images acquired in step 820 are divided by the pixel values of the calibration image acquired under the same illumination, providing a calibrated measurement of reflectance of heart wall tissue in the image. Then, the image is segmented with an algorithm that identifies all pixels with intensities greater than a cut-off value, such as reflectance over 0.13 in the 460-540 nm range, as representing ablated regions.

Similar to the calibrated reflectance measurement, calibrated fluorescence measurements are taken in some embodiments. Instead of a white standard reflectance surface, a fluorescent standard is used. For example, images could simply be added or averaged at block 850. In some embodiments where reflectance at 500 nm and fluorescence at 580 nm both correspond to ablation, the pixel values in these images are averaged to generate a combined image emphasizing ablated areas.

In some cases, images may also be subtracted as part of the combination at step 850. For example, because the slope of the reflectance spectra increases from 590 to 750 nm with increasing ablation, an algorithm in one embodiment subtracts pixel values of reflectance at 590 nm from those at 750 nm. The resulting image would represent the change of the spectra between the two values, which corresponds to the degree of ablation. This method also subtracts out differences in the baseline reflectance and could reduce the need for calibration Certain embodiments employ unsupervised algorithms for characterizing tissue. In some cases, the algorithm is trained to recognize ablations for each individual, for each region of the heart, or both. For instance, an operator can begin by imaging reference regions considered to be ablated and un-ablated. An apparatus such as noted above measures the reflectance and fluorescence properties of the reference regions, and stores these reference values. Subsequently, the apparatus collects reflectance and fluorescent images of the heart wall, and classifies tissue as ablated or non-ablated, depending upon whether the pixel values of the images were closer to ablated or non-ablated tissue. A supervised classification algorithm, using data from one spectral or fluorescent band, could also be used in step 840 to segment ablated and non-ablated regions.

Various blocks, modules or other circuits may be implemented to carry out one or more of the operations and activities described herein and/or shown in the figures. In these contexts, a "block" (also sometimes "logic circuitry" or "module") is a circuit that carries out one or more of these or related operations/activities (e.g., illuminating, collecting light, or processing/displaying light). For example, in certain of the above-discussed embodiments, one or more modules are discrete logic circuits or programmable logic circuits configured and arranged for implementing these operations/activities, as in the circuit modules shown in FIG. 1. In certain embodiments, such a programmable circuit is one or more computer circuits programmed to execute a set (or sets) of instructions (and/or configuration data). The instructions (and/or configuration data) can be in the form of firmware or software stored in and accessible from a memory (circuit). As an example, first and second modules include a combination of a CPU hardware-based circuit and a set of instructions in the form of firmware, where the first module includes a first CPU hardware circuit with one set of instructions and the second module includes a second CPU hardware circuit with another set of instructions.

Certain embodiments are directed to a computer program product (e.g., nonvolatile memory device), which includes a machine or computer-readable medium having stored thereon instructions which may be executed by a computer (or other electronic device) to perform these operations/activities.

Based upon the above discussion and illustrations, those skilled in the art will readily recognize that various modifications and changes may be made to the various embodiments without strictly following the exemplary embodiments and applications illustrated and described herein. For example, a variety of combinations of simulation light wavelengths may be used, and fluorescent responses can be combined with multispectral reflection. In addition, the various embodiments described herein may be combined in certain embodiments, and various aspects of individual embodiments may be implemented as separate embodiments. Such modifications do not depart from the true spirit and scope of various aspects of the invention, including aspects set forth in the claims.

What is claimed is:

1. An apparatus comprising:
   a light source including an array of light emitters configured and arranged to illuminate a tissue region of a heart wall with light at a plurality of different wavelength ranges;
   a light collector configured and arranged to operate in conjunction with the light source to collect a plurality of multispectral images, including respective images of the tissue region of the heart collected at each of the different wavelength ranges at which the tissue region is illuminated by the light source, the plurality of multispectral images further including both reflected light from the tissue region in the plurality of different wavelength ranges and fluorescent light emitted by the tissue region;
   a catheter configured and arranged with the light source and the light collector to position the light source and light collector proximate the tissue region of the heart wall for respectively illuminating the tissue region and collecting the multispectral images and to apply ablation energy to at least a portion of the tissue region of the heart wall; and
   a display circuit configured and arranged to collect and display at least one image depicting a condition of the health of the heart wall tissue region, the at least one image including a visual distinction of scarred tissue from unscarred tissue or ablated tissue from tissue that is not ablated from the applied ablation energy, based on intensities of the reflected light and the fluorescent light as depicted in the respective images of the tissue region collected at each of the different ones of the wavelength ranges, wherein the catheter, the light source and the light collector are configured and arranged to operate with the light source and light collector positioned proximate the tissue region of the heart wall by illuminating the tissue region and collecting the multispectral images and with ablation energy applied to at least a portion of the tissue region of the heart wall, while the display circuit collects and displays said at least one image.

2. The apparatus of claim 1, wherein the display circuit is configured and arranged with the catheter, light source and light collector to collect and display the at least one image depicting a condition of the health of the heart wall tissue region by combining intensities of the reflected light and fluorescent light emitted by the tissue region responsive to the illumination at each of the different wavelength ranges and displaying an image that visually distinguishes scarred tissue from unscarred tissue, or that visually distinguishes ablated tissue from tissue that is not ablated, via the combined intensities.

3. The apparatus of claim 1, wherein the plurality of different wavelengths include four or more different bands of light, wherein the light source is configured and arranged to illuminate the tissue region with pulses of light, each pulse being of one of the plurality of different wavelengths, and wherein the light collector is configured and arranged with the light source to collect each of the multispectral images by, for each of the pulses of light, collecting an image of the tissue region as illuminated with the pulse of light.

4. The apparatus of claim 1, wherein
the light source is configured and arranged to illuminate the tissue region with pulses of light via sequential transmissions of the plurality of different wavelengths, each pulse being a different one of the plurality of different wavelengths,
the light collector is configured and arranged with the light source to collect each of the multispectral images at each of the plurality of different wavelength ranges by, for each of the pulses of light, collecting an image of the tissue region as illuminated with the pulse of light of the respective one of the plurality of different wavelengths, and
the display circuit is configured and arranged to display the at least one image depicting a condition of the health of the heart wall tissue region by combining portions of the respective images obtained for each pulse of light.

5. The apparatus of claim 1, wherein the display circuit is configured and arranged with the catheter, light source and light collector to collect and display the at least one image depicting a condition of the health of the heart wall tissue region by identifying a region of interest in one of the respective images, and displaying an image that visually distinguishes scar tissue from unscarred tissue by combining intensities of the region of interest from a plurality of the respective images, wherein scar tissue reflects light with a higher intensity than unscarred tissue.

6. The apparatus of claim 5, wherein combining intensities of the region of interest from a plurality of the respective images includes adding intensities of the region of interest as depicted in the plurality of respective images, and subtracting intensities of regions of the plurality of respective images that do not include the region of interest, the combined intensities of the region of interest being indicative of a type of tissue from which the light reflects.

7. The apparatus of claim 1, wherein the light source and light collector are configured and arranged to illuminate and collect light from the tissue region using wavelengths of light that reflect from scar tissue with a higher intensity relative to unscarred tissue.

8. The apparatus of claim 1,
further including an ablation electrode, configured to deliver energy at specified energy levels, and configured and arranged to ablate portions of the heart wall while the light source is active, and
wherein the light collector and catheter are configured and arranged with the light source to facilitate collection of light for, in response to the light emitted from the light source, the respective images from the heart wall, thereby providing an indication of the portions of the heart wall having been subjected to ablation.

9. The apparatus of claim 1, wherein
the light source is configured and arranged to effect a fluorescent light response from the tissue region by illuminating the tissue region with light that stimulates the tissue region to generate the fluorescent light,
the light collector is configured and arranged to collect both the reflected light from the tissue region and the fluorescent light emitted by the tissue region, and
the catheter and display circuit are respectively configured and arranged to collect the fluorescent light and display the at least one image based on both the reflected light and the fluorescent light.

10. The apparatus of claim 1, wherein the display circuit is configured and arranged to detect the intensity of reflected light that forms the multispectral images and to provide an indication of scarred tissue based on an expected intensity of light to be reflected from unscarred heart tissue at the respective wavelength ranges and the detected intensity of the reflected light.

11. The apparatus of claim 1, wherein:
the different wavelength ranges include wavelengths in at least one of ultraviolet, visible, and infrared spectra; and
the display circuit is configured and arranged with the light collector to generate a differential image representing a difference of the reflected light in respective images collected under the different wavelength ranges by mathematically combining the respective images.

12. The apparatus of claim 1, wherein the display circuit is configured and arranged to depict the condition of the health of the heart wall tissue region by depicting an indication of increased reflectance corresponding to ablated tissue.

13. The apparatus of claim 1, wherein the display circuit is configured and arranged with the light collector to display an image depicting a condition of ablation based on a difference in reflectance of respective wavelength ranges, by indicating tissue having been ablated as portions of the displayed image exhibiting greater differences in reflectance.

14. A method comprising:
illuminating a tissue region of a heart wall, by using a light source, with light at a plurality of different wavelength ranges;
collecting a plurality of multispectral images, by using a light collector, including respective images collected at each of the plurality of different wavelength ranges at which the tissue region is illuminated; and collecting and displaying, using a circuit, at least one image depicting a condition of the health of the heart wall tissue region, based on the respective images collected at the different ones of the plurality of wavelength ranges, wherein illuminating the tissue region and collecting the plurality of multispectral images include positioning the light source and the light collector with a catheter proximate the tissue region of the heart wall for respectively illuminating the tissue region and collecting the multispectral images, and wherein the light source and the light collector are positioned proximate the tissue region of the heart wall and therein illuminate the tissue region and collect the multispectral images and ablation energy is applied to at least a portion of the tissue region of the heart wall, while the circuit is positioned with the light source and the light collector to collect and display said at least one image.

15. The method of claim 14, wherein collecting and displaying the at least one image depicting a condition of the health of the heart wall tissue region includes combining intensities of ones of the respective images and displaying an image that visually distinguishes scarred tissue from unscarred tissue, or that visually distinguishes ablated tissue from tissue that is not ablated, via the combined intensities, by generating a differential image representing a difference of the reflectance in the respective images collected under different wavelength ranges.

16. The method of claim 14, wherein
illuminating the tissue region of the heart wall, by using the light source, includes illuminating the tissue region with pulses of light, each pulse being of one of the plurality of different wavelength ranges, and
collecting the plurality of multispectral images, by using the light collector, includes collecting, for each of the pulses of light, an image of the tissue region as illuminated with the pulse of light.

17. The method of claim 16, wherein collecting and displaying the at least one image includes combining portions of the respective images obtained for each pulse of light and displaying the combined portions.

18. The method of claim 14, wherein
illuminating the tissue region of the heart wall, by using the light source, with light at a plurality of different wavelength ranges includes illuminating the tissue region of the heart wall, by using the light source, with light having a wavelength that reflects from scar tissue with a higher intensity relative to unscarred tissue, relative to other wavelengths of light, and
collecting and displaying the at least one image includes collecting light from the tissue region and using the higher intensity of the light reflecting from scar tissue to identify the scar tissue in the at least one image.

19. The method of claim 14, wherein collecting and displaying the at least one image includes identifying a region of interest in one of the respective images, adding intensities of the region of interest as depicted in the plurality of respective images, and
subtracting intensities of regions of the plurality of respective images that do not include the region of interest.

20. The method of claim 14, wherein
illuminating the tissue region of the heart wall, by using the light source, includes inducing a fluorescent light response from the tissue region by illuminating the tissue region with light that stimulates the tissue region to generate the fluorescent light response,
collecting the plurality of multispectral images, by using the light collector, includes collecting both reflected light from the tissue region and fluorescent light emitted by the tissue region, and
collecting and displaying include collecting the fluorescent light and displaying the at least one image based on both the reflected light and the fluorescent light.

21. An apparatus comprising:
a light source including an array of light emitters configured and arranged to induce a fluorescent response from a tissue region of a heart wall by illuminating the tissue region with light at a plurality of different wavelength ranges;
a filter configured and arranged to block reflected light;
a light collector configured and arranged to collect images of the fluorescent response of the tissue region as the tissue region is sequentially illuminated with light at the respective wavelength ranges, the wavelength of the fluorescent response being longer than the wavelengths of the illumination light;
a catheter configured and arranged with the light source and the light collector to position the light source and light collector proximate the tissue region of the heart wall for respectively illuminating the tissue region and collecting the fluorescent response; and
a display circuit configured and arranged to collect and display at least one image depicting a condition of the health of the heart wall tissue region, based on the collected images; wherein the catheter, the filter, the light source and the light collector are configured and arranged to operate with the light source and light collector positioned proximate the tissue region of the heart wall by illuminating the tissue region and collecting multispectral images and with ablation energy applied to at least a portion of the tissue region of the heart wall, while the display circuit collects and displays said at least one image.

* * * * *